United States Patent [19]

Eckerle

[11] Patent Number: 4,802,488
[45] Date of Patent: Feb. 7, 1989

[54] BLOOD PRESSURE MONITORING METHOD AND APPARATUS

[75] Inventor: Joseph S. Eckerle, Redwood City, Calif.

[73] Assignee: SRI International, Menlo Park, Calif.

[21] Appl. No.: 7,038

[22] Filed: Jan. 27, 1987

Related U.S. Application Data

[63] Continuation-in-part of Ser. No. 927,843, Nov. 6, 1986.

[51] Int. Cl.$^4$ .............................................. A61B 5/02
[52] U.S. Cl. ..................................... 128/672; 128/690
[58] Field of Search ........................ 178/672, 677–683, 178/687–690

[56] References Cited

U.S. PATENT DOCUMENTS

| | | | |
|---|---|---|---|
| 3,123,068 | 3/1964 | Bigliano | 128/2.05 |
| 3,219,035 | 11/1965 | Pressman et al. | 128/2.05 |
| 3,880,145 | 4/1975 | Blick | 128/672 |
| 4,262,675 | 4/1981 | Kubo et al. | 128/680 |
| 4,269,193 | 5/1981 | Eckerle | 128/672 |
| 4,271,843 | 6/1981 | Flynn | 128/681 |
| 4,409,983 | 10/1983 | Albert | 128/689 |
| 4,423,738 | 1/1984 | Newgard | 128/672 |
| 4,638,810 | 1/1987 | Ramsey, III et al. | 128/681 |
| 4,669,485 | 6/1987 | Russell | 128/679 |

OTHER PUBLICATIONS

Pressman, G. L. et al., "A Transducer for the Continuous External Measurement of Blood Pressure", IEEE Trans. Bio-Med. Elec., Apr. 1963, pp. 73–81.
C. S. Weaver et al. "A Study of noninvasive blood pressure measurement techniqes", pp. 89–105 (see pp. 89–90 and 93–97, and FIGS. 2, 20–23) Conference held at Stanford University, Sept. 1978, Soc. of Photo-Optical Instrumentation Engineers (Bellingham, U.S.).

Primary Examiner—Francis Jaworski
Assistant Examiner—George Manuel
Attorney, Agent, or Firm—Victor R. Beckman

[57] ABSTRACT

Intraarterial blood pressure is measured noninvasively by an electromechanical transducer (22) that includes an array of transducer elements (22-1 through 22-19). The transducer extends across an artery (24) with transducer elements at the ends of the array extending beyond opposite edges of the artery. A set of diastolic and/or systolic pressure and pulse amplitude values is obtained from the outputs from the transducer elements, which values are stored in computer (62). Information concerning the subject related to the diameter of the underlying artery including, for example, the subject's age, weight, arm and wrist diameter also is entered into computer (62) through keyboard (64), from which information an estimation of the diameter of the underlying artery is obtained. Using the set of pulse amplitude values, a transducer element at the center of a search area located substantially at the center of the artery is identified. A center of gravity, a two humps and/or a curve fitting method may be used to identify the transducer element at the center of the search area. A group of transducer elements that overlies the artery of estimated diameter then is identified. Using outputs from only said group of transducer elements, one transducer element having a local minimum of one of the diastolic and systolic pressures, relative to the transducer at the center of the search area, is identified, which transducer element is selected for monitoring blood pressure.

15 Claims, 8 Drawing Sheets

BLOOD PRESSURE MONITORING METHOD AND APPARATUS

ORIGIN OF THE INVENTION

The invention described herein was made in the course of work under a grant or award from the Department of Health and Human Services.

RELATED APPLICATIONS

This application is a continuation-in-part of Ser. No. 927,843, filed Nov. 6, 1986, entitled Blood Pressure Monitoring Method and Apparatus.

TECHNICAL FIELD

This invention relates to method and apparatus for non-invasively monitoring blood pressure through use of a transducer array of individual pressure or force sensing elements, and to method and means for selecting the one pressure sensitive element which most closely tracks the true blood pressure waveform and gives the most accurate measure of blood pressure.

BACKGROUND OF THE INVENTION

The continuous measurement of blood pressure by use of arterial tonometer transducers is well known as shown in U.S. Pat. Nos. 3,123,068 to R. P. Bigliano, 3,219,035 to G. L. Pressman, P. M. Newgard, and in John J. Eige, 3,880,145 to E. F. Blick, 4,269,193 to the present invention, and 4,423,738 to P. M. Newgard, and in an article by G. L. Pressman and P. M. Newgard entitled "A Transducer for the Continuous External Measurement of Arterial Blood Pressure" (IEEE Trans. Bio-Med. Elec., Apr. 1963, pp. 73-81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array have at least one dimension smaller than the lumen of the underlying artery in which blood pressure is measured, and the transducer is positioned such that more than one of the individual pressure-sensitive elements is over at least a portion of the underlying artery. The output from one of the pressure sensitive elements is selected for monitoring blood pressure. The element that is substantially centered over the artery has a signal output that provides an accurate measure of intraarterial blood pressure. However, for the other transducer elements the signal outputs generally do not provide as accurate a measure of intraarterial blood pressure as the output from the centered element. Generally, the offset, upon which systolic and diastolic pressures depend, will not be measured accurately using transducer elements that are not centered over the artery. In some prior art arrangements, the pressure sensitive element having the maximum pulse amplitude output is selected, and in other arrangements the element having a local minimum of diastolic or systolic pressure which element is within substantially one artery diameter of the element which generates the waveform of maximum pulse amplitude is selected. The latter method is shown in the above-mentioned J.S. Eckerle U.S. Pat. No. 4,269,193. The selection method disclosed in U.S. Pat. No. 4,269,193 generally identifies the correct transducer element to be used. However, pressure readings provided by individual elements of a transducer array may not be perfectly accurate due to any number of factors. Even small errors in the pressure readings may result in the selection of an incorrect transducer element using the system disclosed in U.S. Pat. No. 4,269,193, in which case the blood pressure measurements are inaccurate.

SUMMARY AND OBJECTS OF THE INVENTION

An object of this invention is the provision of an improved tonometric type method and apparatus for non-invasively monitoring blood pressure with a high degree of accuracy.

Another object of this invention is the provision of such a blood pressure measuring method and apparatus which includes the use of a transducer having an array of individual transducing arterial riders (pressure sensitive elements) and wherein means are provided for selecting the element which most closely reproduces the actual blood pressure waveform.

The present invention includes an array of individual pressure sensitive elements, each of which elements have at least one dimension smaller than the lumen of the underlying artery in which blood pressure is measured. The elements are of sufficiently small size such that with the array positioned so as to extend across the artery a plurality of elements are located over the artery. Of course, the number of elements located over the artery will depend upon the artery diameter. Generally, artery diameter is related to the subject's sex, height, weight, age, arm and/or wrist dimension, or like anatomical or physiological attributes of the subject. For example, the diameter of a child's artery generally is smaller than that of an adult, and arteries of females generally are smaller than those of males.

In accordance with the present invention, outputs of all of the transducer elements are employed in locating the center of a search area which, ideally, is centrally located over the artery. Novel means, described below, are used to locate the transducer element to be used as the center of the search area. Then, outputs from a limited number of transducer elements are employed in selecting that element within the limited-number group which is to be used for obtaining blood pressure measurements. The number of transducer elements within the group of elements to be searched is dependent upon one or more anatomical or physiological attributes of the subject, such as mentioned above. The pressure sensitive element within the limited-number group that has a local minimum of at least one of diastolic and systolic pressures is selected as the element to use for monitoring blood pressure.

Novel methods for locating the center of the search area include use of measurements of pulse amplitude. The difference between the systolic and diastolic pressure values is defined herein as the pulse amplitude of the blood pressure waveform. For many subjects, the graph of pulse amplitude versus transducer element (of the array of elements) includes two humps, or peaks, of substantially equal magnitude at the transducer elements which overlie the two edges of the artery. One novel method of this invention involves locating the transducer element that is midway between the two humps, which element then is taken as the center of the search area. A pair of local maxima may be found from the pulse amplitude values derived from outputs from the transducer elements of the array. Then, the transducer element centered between the elements with the local maxima is identified as the element at the center of the search area.

Another novel means for locating the center of the search area includes fitting a polynomial of at least second order to the pulse amplitude values from the elements of the array. The element at which the pulse amplitude curve is maximum is selected as the element at the center of the search area. Further novel means for locating the center of the search area includes computing the center of gravity of the graph of pulse amplitude versus transducer element, with the element at the center of gravity being selected as the element at the center of the search area.

BRIEF DESCRIPTION OF THE DRAWINGS

The invention, together with the above and other objects and advantages thereof will be better understood from the following description when considered with the accompanying drawings. It will be understood, however, that the illustrated embodiments of the invention are by way of example only and that the invention is not limited thereto. The novel features which are believed to be characteristic of the invention ar set forth with particularity in the appended claims. In the drawings, wherein like reference characters refer to the same parts in the several views:

Figure 1:
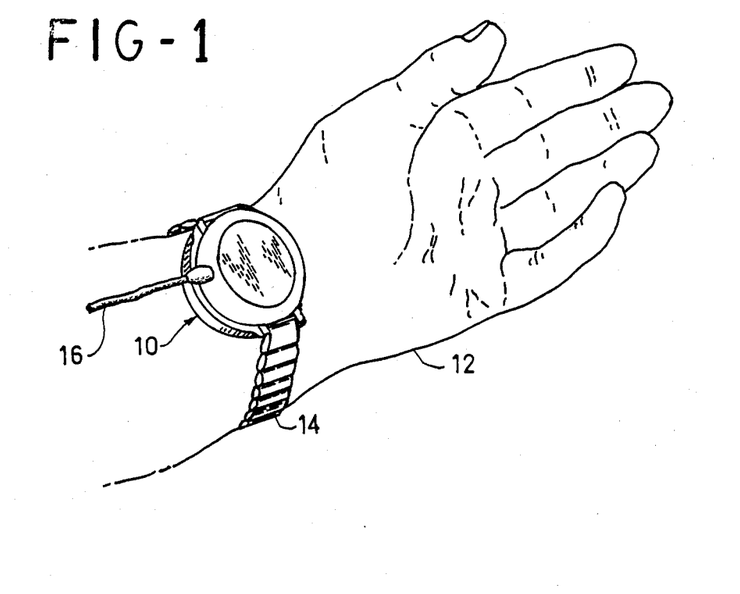
FIG. 1 shows the external appearance of a blood pressure transducer case, typically positioned over an artery, for providing a continuous external measurement of arterial blood pressure.
Figure 3:
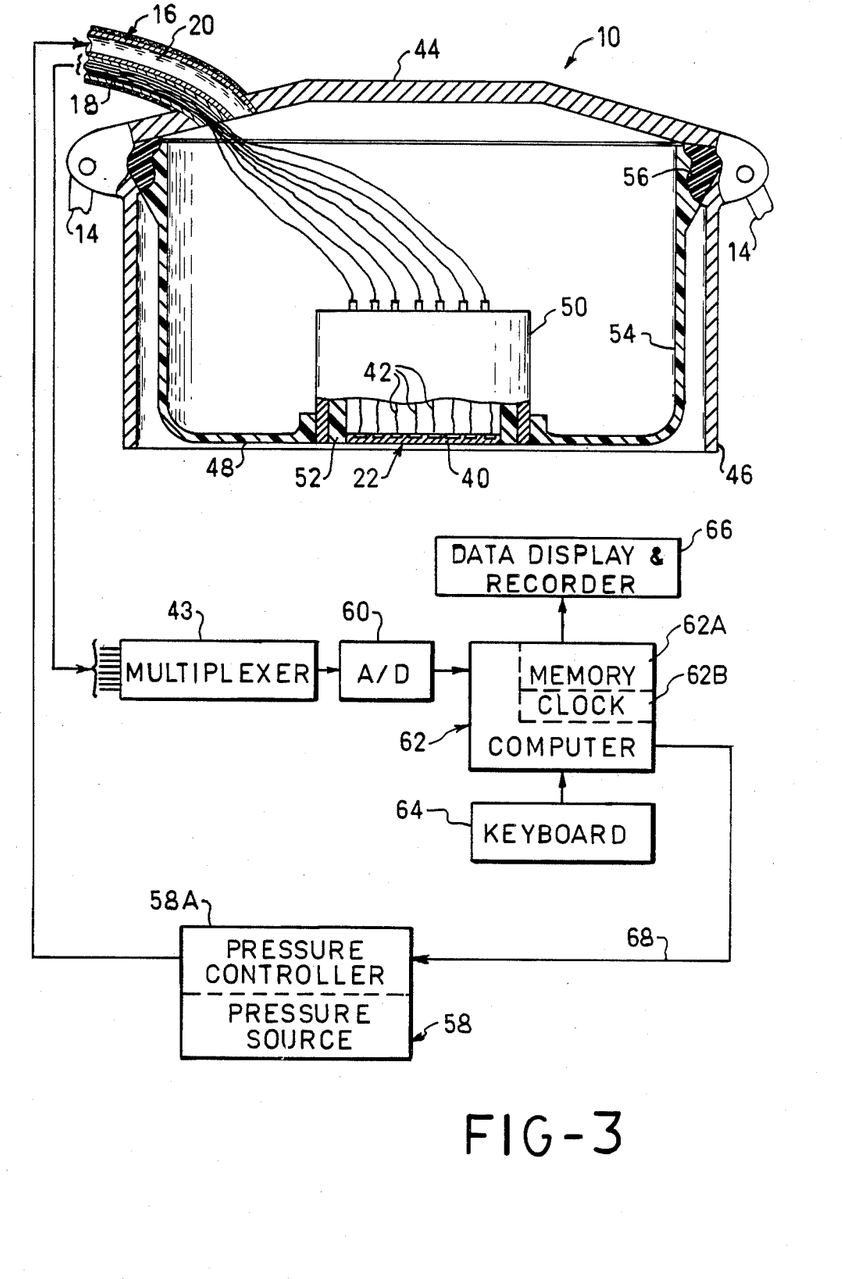
FIG. 3 is a combination simplified vertical sectional view taken through the transducer case of FIG. 1 and block diagram of a system which may be employed therewith in the practice of this invention.

A typical application of the transducer array for arterial tonometry is illustrated in FIG. 1 wherein the transducer housing, or case, 10 which have the appearance of an ordinary wristwatch case, is held in place over the radial artery in a human wrist 12 by a band 14. A cord 16 extends from the transducer housing 10 through which electrical wiring for the transducer array within the housing, together with a small tube that connects the housing to an air pressure source, extend. The wiring 18 and tube 20 are shown in FIG. 3, but not in FIG. 1.

Figure 2:
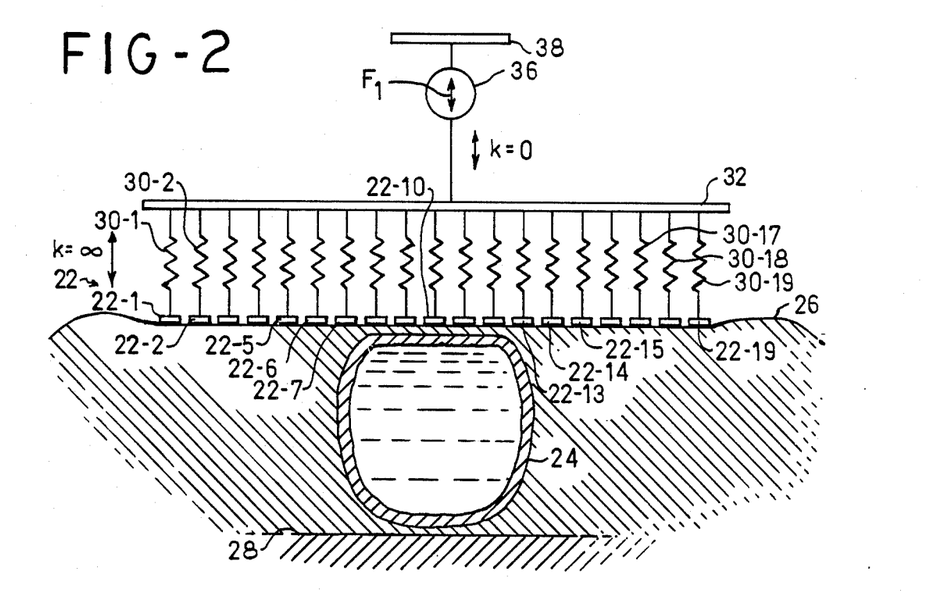
FIG. 2 is a schematic diagram illustrating the force balance between the artery and the multiple tranducer elements (arterial riders), with the artery wall properly depressed to give accurate blood pressure readings.

Reference now is made to FIG. 2 wherein a diagrammatic mechanical model is shown which is representative of factors to be considered in the physical system. The illustrated model is that shown in the above-mentioned J. S. Eckerle U.S. Pat. No. 4,269,193 which was adapted from the G. L. Pressman and P. M. Newgard article entitled "A Transducer for the Continuous External Measurement of Arterial Blood Pressure". In brief, an array 22 of individual pressure sensitive elements or transducers 22-1 through 22-19 which constitute the arterial riders, is positioned so that one or more of the riders are entirely over an artery 24. The individual riders 22-1 through 22-19 are small relative to the diameter of the artery 24 thus assuring that a plurality of the riders overlie the artery. The skin surface 26 and artery underlying the transducer must be flattened by application of a holddown pressure to the transducer. One rider overlying the center of the artery is identified as the "centered" rider, from which rider pressure readings for monitoring blood pressure are obtained. The present invention is directed to novel method and means for selecting the "centered" rider, and is described in detail hereinbelow. For present purposes it will be understood that by using the rider selecting means of this invention, one of the riders, such as rider 22-10, may be selected as the "centered" rider, in which case the remainder of the riders, here riders 22-1 through 22-9 and 22-11 through 22-19 comprise "side plates" which serve to flatten the underlying skin and artery. Depending upon the positioning of the transducer on the subject, a different transducer element may be positioned over the center of the artery and be selected as the "centered" rider.

Superficial arteries, such as the radial artery, are supported from below by bone which, in FIG. 2 is illustrated by ground symbol 28 under the artery. The wall of artery 24 behaves substantially like a membrane in that it transmits tension forces but not bending moments. The artery wall responds to the loading force of the transducer array, and during blood pressure measurements acts as if it is resting on the firm base 28. The effective stiffness of an artery wall is small and differs between subjects. In prior art mechanical models of the physical system, the effective stiffness of the artery wall is taken as zero, in which case the actual hold-down pressure employed is not considered to affect accuracy of the blood pressure readings so long as the transducer is pressed against the skin surface with sufficient force to cause compression but not occlusion of the underlying artery. Applicant has found that not only are blood pressure readings dependent upon hold-down pressure within the range of hold-down pressures for which the artery is flattened but not occluded, but that most accurate blood pressure readings are obtained when a hold-down pressure is selected that is substantially midway between the pressure at which flattening of the artery begins and the minimum pressure required for occluding the same. Novel steps involved in computing the correct hold-down pressure are described in detail in the above-mentioned U.S. patent application Ser. No. 927,843.

With the illustrated system, the transducer case 10 and mounting strap 14, together with air pressure applied to a bladder 54, supply the required compression force and hold the riders 22-1 through 22-19 in such a manner that arterial pressure changes are transferred to the riders which overlie the artery 24. This is illustrated schematically in FIG. 2 by showing the individual riders 22-1 through 22-19 backed by rider spring members 30-1 through 30-19, respectively, a rigid spring backing plate 32, and hold-down force generator 36 between the backing plate 32 and the mounting strap system 38.

If, without force generator 36, the coupling between the mounting strap system 38 and spring backing plate 32 were infinitely stiff to restrain the riders 22-1 through 22-19 rigidly with respect to the bone structure 28, the riders would be maintained in a fixed position relative to the artery. In practice, however, such a system is not practical, and hold-down force generator 36, comprising (in the present example) a pneumatic loading system, is included to keep constant the force applied by the mounting strap system 38 to riders 22-1 through 22-19. In the mechanical model the spring constant, k (force per unit of deflection) of the force generator, 36, is nearly zero. Suitable pneumatic loading systems are shown and described in the above-referenced U.S. Pat. Nos. 3,219,035 and 4,269,193, and the Pressman and Newgard IEEE article.

In order to insure that the riders 22-1 through 22-19 flatten the artery and provide a true blood pressure measurement, they must be rigidly mounted to the backing plate 32. Hence, the rider springs 30-1 through 30-19 of the device ideally are infinitely rigid (spring constant $k = \infty$). It is found that as long as the system operates in such a manner that it can be simulated by rider springs 30-1 through 30-19 having a spring constant on the order of about ten times the corresponding constant for the artery-skin system, so that the deflection of riders 22-1 through 22-19 is small, a true blood pressure measurement may be obtained when the correct hold-down pressure is employed.

The actual physical structure of a practical transducer of a type which may be employed for transducer array 22 in the present system is shown in the above-mentioned J. S. Eckerle U.S. Pat. No. 4,269,193. There, a transducer array is shown in which the individual transducers (riders) are formed in a thin monocrystalline silicon substrate which is made using integrated circuit fabrication techniques. In FIG. 3, to which reference now is made, a simplified showing of transducer 22 is shown comprising a chip 40 which includes an array of individual transducers, not shown. Electrical conductors 42 connect the individual transducers to the wiring 18 for connection thereof to a multiplexer 43.

As seen in FIG. 3, case 10 comprises a generally cylindrical, hollow, container having rigid back and side walls 44 and 46, respectively. The silicon transducer chip 40 is mounted within the face 48 of the case (designated as the front or operative face) in a cylindrical cup-like transducer housing 50. The operative face 48 includes the silicon transducer chip 40 along with its included individual transducers and arterial riders. Chip 40 may be affixed to a conventional ceramic dual in-line package that is plugged into an associated dual in-line socket, neither of which are shown in the drawings. A silicone rubber filler 52 is provided inside the housing 50 and around the dual in-line package and socket to provide a good seal, prevent electrical leakage between the transducer circuits and housing 50, and provide a flat surface to press against the subject. The front face 48 of the transducer includes the lower faces of housing 50 and filler 52.

The transducer housing 50 is fixed to the inside of the transducer case 10 by means of a cup-like silicone rubber bladder 54 which is sealed around the lower outside lip of the cup-shaped transducer housing 50, extends upwardly inside the outer wall of the transducer case 10, and is sealed to a ring 56, which in turn is fixed and sealed to the inside back of the transducer case 10. A chamber is formed inside the bladder which is connected to an air pressure source 58 through tube 20. A pressure controller 58A may be included in the pressure source. Since the flexible bladder 54 is sealed both to the transducer housing 50 and the inside of the transducer case 10, air under pressure from source 58 pneumatically loads the operative face 48. With the transducer strapped to the subject's wrist, the hold-down force $F_1$ exerted by the transducer array against the skin of the subject is adjustable by control of the air pressure. (In the diagrammatic mechanical model shown in FIG. 2 the hold-down force $F_1$ is generated by hold-down force generator 36.)

As noted above, electrical signals related to pressure sensed by the individual transducers 22-1 through 22-19 of transducer 22 are supplied as inputs to an analog multiplexer 43. From the multiplexer, the signals are digitized by an analog-to-digital (A-D) converter 60, and the digitized signals are supplied to a digital computer 62 having memory 62A and a clock 62B. Other information, such as the subject's name, sex, weight, height, age, arm and wrist dimensions, and the like, are supplied to the computer through user information input means such as a a keyboard 64. As described hereinbelow, this information is used to make an estimate of the diameter of the artery of the subject, which then is used to establish the range of transducer elements that will be employed in selecting the "centered" rider after the center of the search region has been established.

Output from the computer is supplied to data display and recorder means 66 which may include a recorder, cathode ray tube monitor, a solid state display, or the like. If the desired, at least a portion of the visual display may be included in transducer case 10. Obviously, the computer output may be supplied to a printer, an audible alarm, or the like, as desired. Also, an output from the computer is supplied over line 68 to the pressure controller for control of the transducer hold-down pressure.

Figure 4:
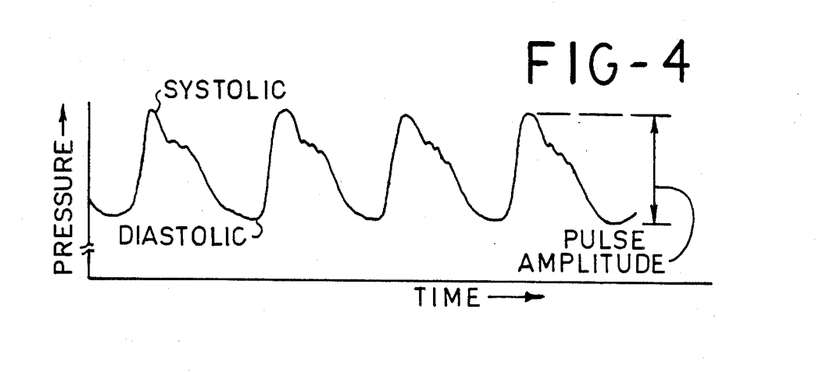
FIG. 4 is a waveform of human blood pressure versus time of the type which may be obtained using the present invention for illustrating systolic and diastolic pressures and pulse amplitude of the blood pressure wave.

In FIG. 4, to which reference now is made, the signal waveform of the output from one of the pressure sensitive elements 22-1 through 22-19 which overlies artery 24 is shown. Other elements of the transducer array which overlie the artery will have waveforms of similar shape. With a correct hold down pressure and correct selection of the "centered" arterial rider (i.e. the rider substantially centered over the artery) the waveform is representative of the blood pressure within the underlying artery. Systolic, diastolic and pulse amplitude pressures are indicated on the waveform, wherein pulse amplitude is the difference between the systolic and diastolic pressures for a given heartbeat.

OVERALL SYSTEM OPERATION

Figure 5A:
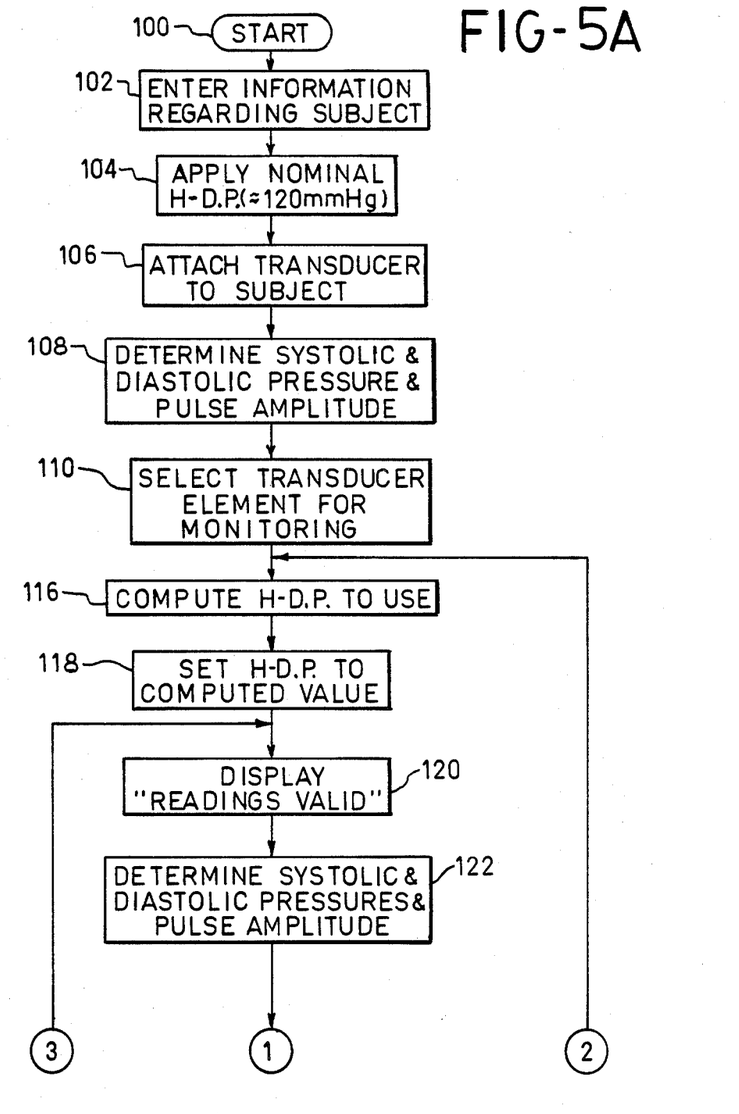
FIGS. 5A and 5B together show a flow chart for use in explaining overall operation of this invention.
Figure 5B:
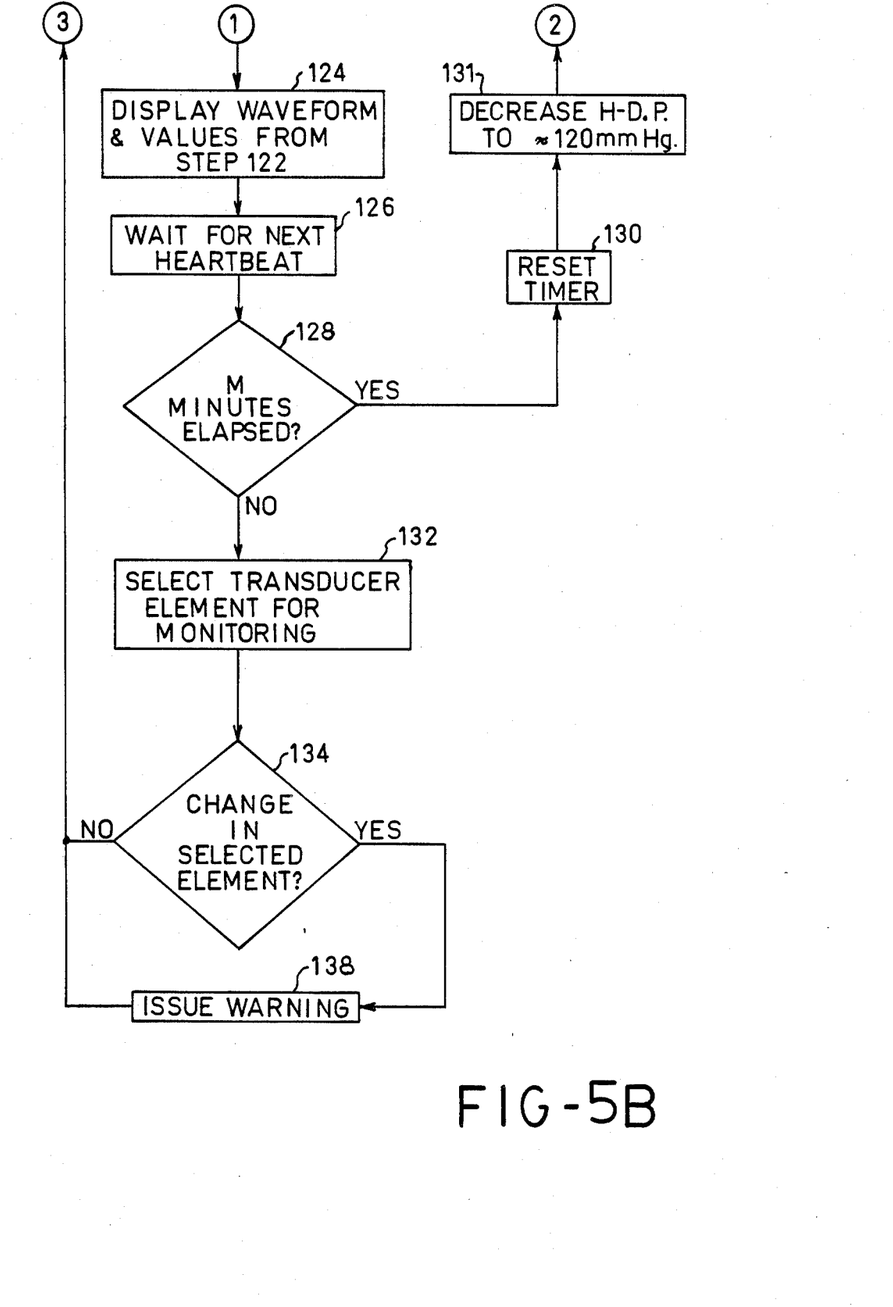

FIGS. 5A and 5B, together show a flow chart of an algorithm for general, overall, operation of the blood pressure monitoring system. Some of the operations indicated therein are under control of computer 62 responsive to programming instructions contained in memory unit 62A. Obviously, several program steps may be involved in the actual implementation of the indicated operations. Since the programming of such steps is well within the skill of the average programmer, a complete program listing is not required and is not included herein.

Preparation for monitoring is begun at START step 100 at which time system power is turned on or a reset operation is performed, by means not shown, and counters, registers, timers, and the like in computer 62 are initialized. At step 102 information concerning the subject, such as the subject's sex, weight, height, age, arm and/or wrist dimensions, and the like, is entered into the computer memory through use of the keyboard 64. Next, at step 104, a nominal hold-down pressure (H-D.P.) is applied wherein air under pressure from source 58 is supplied to the transducer. For example, a hold-down pressure of say 120 mmHg may be supplied to the transducer, which pressure serves to extend the bladder 54 whereby operative face 48 extends outwardly a short distance from the bottom of the case 10. The transducer is attached to the subject at step 106 at a location wherein a centrally located transducer element, such as element 22-10 of transducer array 22 overlies the center of the artery 24. Of course, the exact position of the transducer array relative to the underlying artery generally is not visually apparent to the subject, or operator, and repositioning of the transducer may be required to properly position the same.

With the transducer attached to the subject, step 108 is entered at which point systolic and diastolic pressures are determined from the outputs of each transducer element, and pulse amplitude values are determined by subtraction of the diastolic pressure values from the systolic pressure values. Step 110 then is entered wherein the transducer element to be used in monitoring blood pressure is selected. Novel algorithms which may be used in selecting the proper transducer element are described in detail hereinbelow. For present purposes, it will be understood that the transducer element that is selected for monitoring will be near the center of the array and will be substantially centered over the underlying artery. As will become apparent hereinbelow, step 110 may require repositioning of the transducer for properly locating it relative to the underlying artery.

Following step 110, the hold-down pressure to use to obtain accurate blood pressure measurements is computed at step 116. Algorithms which may be used in computing the correct hold-down pressure are disclosed in the above-mentioned patent application Ser. No. 927,843, filed Nov. 6, 1986. For purposes of the present application, it will be understood that a correct hold-down pressure for accurate blood-pressure monitoring is computed at step 116, following which, at step 118, the computed hold-down pressure is set by control of pressure controller 58A by the computer 62.

With the transducer properly positioned on the subject and the correct hold-down pressure supplied thereto, the system is in condition for obtaining accurate blood pressure readings. At step 120 an indication that the system is operative is provided, as by display of the words "Readings Valid". Obviously, other displays, such as a green indicator light, may be employed for indicating the operating state of the system.

From the output from the selected transducer element, systolic and diastolic pressure values together with pulse amplitude values are readily determined in step 122. Also, pulse rate is readily calculated by determining the time between successive diastolic or systolic pressures. At step 124, values calculated and determined in step 122 are displayed and/or recorded along with the actual waveform. Obviously, the values which are calculated and displayed depend upon the use to be made of the blood pressure monitor, a display of all of the values not being required in many instances. For example, the blood pressure waveform could be recorded without calculation and display of any of the values identified in step 122.

After one or more of the values identified in step 122 are determined, such as systolic and/or diastolic pressure, step 126 is entered wherein the system waits for the next heartbeat cycle. Diastolic or systolic pressure points may be used to identify reference points in the heartbeat cycles. Decision step 128 then is entered at which time a timer in computer 62 is tested to determine whether or not it has reached a predetermined time "M", where M is a time period of, say, 30 minutes. If the elapsed time exceeds the predetermined time period, M, wherein the decision is affirmative, the timer is reset at step 130, hold-down pressure is reduced to approximately 120 mmHg at step 131, and step 116 is reentered for recomputation of the correct hold-down pressure and resetting thereof, if required. Periodic checking and resetting of hold-down pressure helps to assure continued accuracy of the blood pressure readings.

If the predetermined time period is not exceeded, step 132 is entered for selection of the transducer element to be used for monitoring, which step is substantially the same as step 108 described above. Decision step 134 then is entered in which the selected ("centered") transducer element determined in step 108 (or the previous execution of step 132) is compared to that determined in step 132. If there is no change in selected transducer elements, step 120 is reentered indicating that the readings are valid. However, if there has been a change in the selected transducer element, such that decision step 134 is affirmative, then a warning is issued at step 138 indicating to the subject or operator that movement of the transducer relative to the artery has taken place. If desired, the transducer then may be repositioned and the process restarted. If the transducer is not repositioned, and the process is not terminated and restarted, step 120 is reentered for continuation of the monitoring process, but now using the output from the newly selected "centered" transducer element.

SELECTION OF TRANSDUCER ELEMENT FOR MONITORING

A. In General

Figure 6:
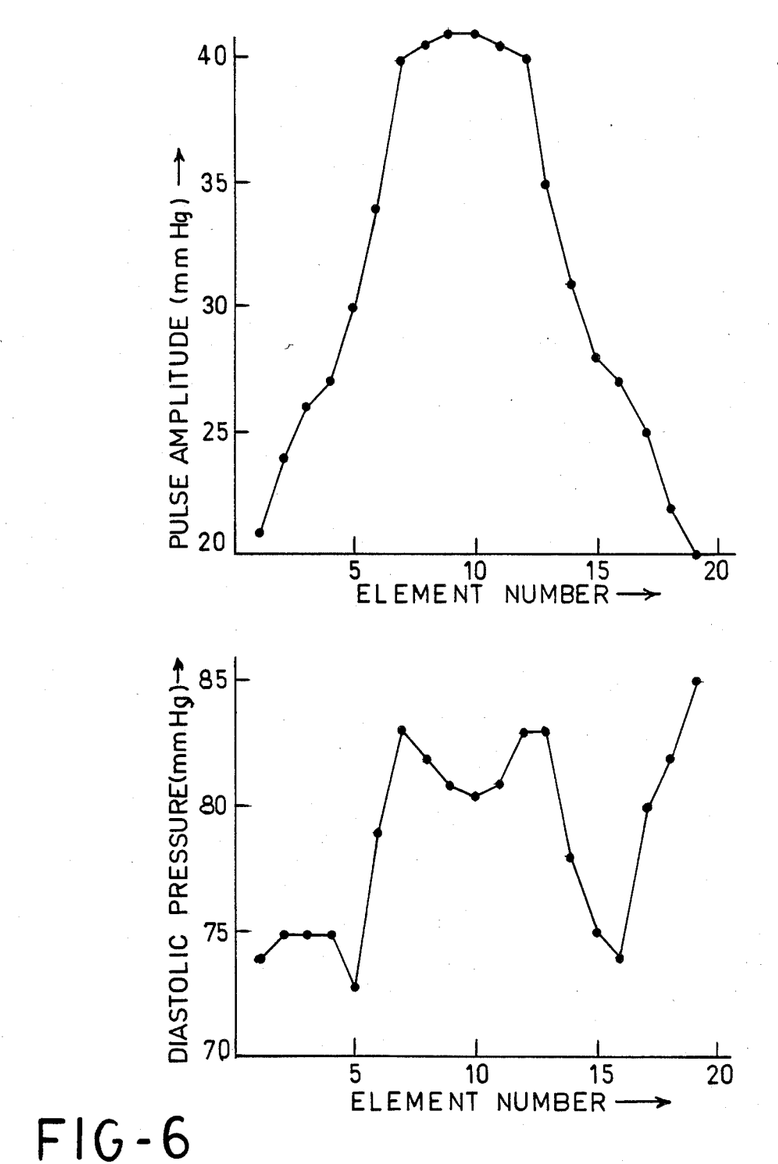
FIG. 6 shows plots of diastolic pressure and pulse amplitude versus transducer element obtained from a subject under ideal conditions.

Reference now is made to FIG. 6 wherein a typical pressure distribution is shown which may be obtained from outputs of transducer elements 22-1 through 22-19 of transducer array 22 placed over superficial artery 24. In FIG. 6 both the distribution of diastolic pressures and the distribution of pulse amplitudes are shown. As noted above, the systolic pressure distribution is very similar to the distribution of diastolic pressures, being displaced vertically by about 40 mmHg. For simplicity, diastolic and pulse amplitude distributions are shown and described. However, for each statement made about diastolic pressures, a similar statement can be made concerning systolic pressures. In the FIG. 6 and FIG. 7 examples, the center of the underlying artery is nearest to transducer element number 10.

When conditions are favorable and the tonometer transducer is extremely accurate, pressure distributions such as those of FIG. 6 will usually be obtained from most subjects. In these cases, algorithms disclosed in U.S. Pat. No. 4,269,193 by J. S. Eckerle will correctly identify and select the transducer element located nearest to the center of the underlying artery. As noted above, in the system shown in U.S. Pat. No. 4,269,193, the transducer element which generates the waveform of maximum pulse amplitude first is identified. In FIG. 6, it will be seen that transducer element 22-10 (element 10 in FIG. 6) has the maximum pulse amplitude output. The transducer element that has a local minimum of diastolic (or systolic) pressure that is within substantially one artery diameter of the transducer element with the maximum pulse amplitude then (following the teachings of U.S. Pat. No. 4,269,193) is selected as the correct element for obtaining blood pressure measurements. In FIG. 6, it will be seen that a local minimum of diastolic pressure is produced at transducer element 22-10 (element 10 in FIG. 6). It will be seen then that the system shown in U.S. Pat. No. 4,269,193 will correctly identify and select the transducer element located nearest the center of the underlying artery when extremely accurate pressure distributions are provided by the tonometer transducer.

Unfortunately, tonometer transducers are not perfectly accurate and various other factors such as electronic noise, round-off or truncation errors, subject movement and poor transducer positioning are experienced in practice. These factors can result in small deviations of the pressure distribution from the "ideal" shown in FIG. 6. Although small, these deviations can cause the aforementioned U.S. Pat. No. 4,269,193 algorithms to select the wrong transducer element leading to inaccurate blood pressure measurements. Improved algorigthms, described hereinbelow, have been devised that are able to correctly identify the transducer element which overlies the center of the underlying artery even if perfectly accurate pressure distributions are not obtained from the transducer array.

Figure 7:
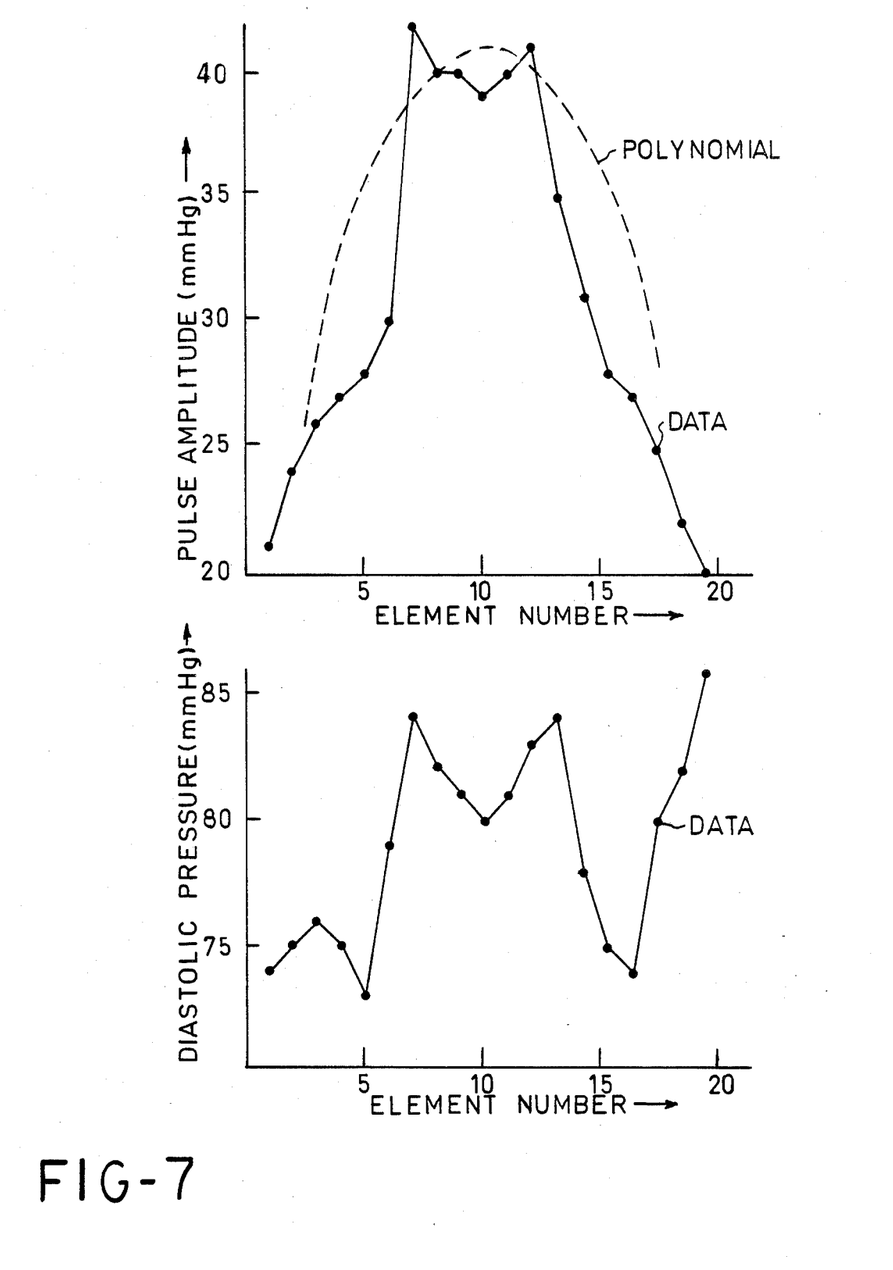
FIG. 7 shows a pressure distribution which is similar to that of FIG. 6 from the same subject but under conditions that are not ideal.

Reference now is made to FIG. 7 wherein, unlike FIG. 6, pressure distributions that are not "ideal" are shown, which distributions are rather common due to the various factors mentioned above. It here will be noted that both the FIG. 6 and 7 distributions are from the same subject. Also, based on the subject's age, sex, wrist size, or the like, it is assumed, or estimated, that the diameter of the underlying artery is about equal to six transducer elements. in the pulse amplitude pressure distributions, it will be seen that the maximum pulse amplitude occurs at element 10 in FIG. 6 and at element 7 in FIG. 7. Using the FIG. 7 pressure distributions and the algorithms of U.S. Pat. No. 4,269,193, element 7 would be identified as having the maximum pulse amplitude, and element 5 would be identified as the transducer element having a local minimum of diastolic pressure. As a result, transducer element 5 would incorrectly be identified as being the "centered" transducer element whereas, in fact, the "centered" transducer element is actually element 10. Thus, it will be seen that the algorithms of U.S. Pat. No. 4,269,193 may lead to erroneous transducer element selection and, consequently inaccurate blood pressure measurements. Novel methods for accurately locating the center of the search region which avoid shortcomings of the algorithms of U.S. Pat. No. 4,269,193 in the presence of small but rather common errors in the pulse amplitude pressure distribution now will be described.

B. Locating Center of Search Region

1. General Considerations

As seen in FIG. 5A, selection of the transducer element for monitoring (step 110) takes place with the transducer attached to the subject (step 106) and with a nominal hold-down pressure of, say, 120 mmHg supplied to the transducer. It here will be noted that during blood pressure monitoring a much larger hold-down pressure generally is employed, often in the range of 150–220 mmHg, as determined in step 116.

Figure 8:
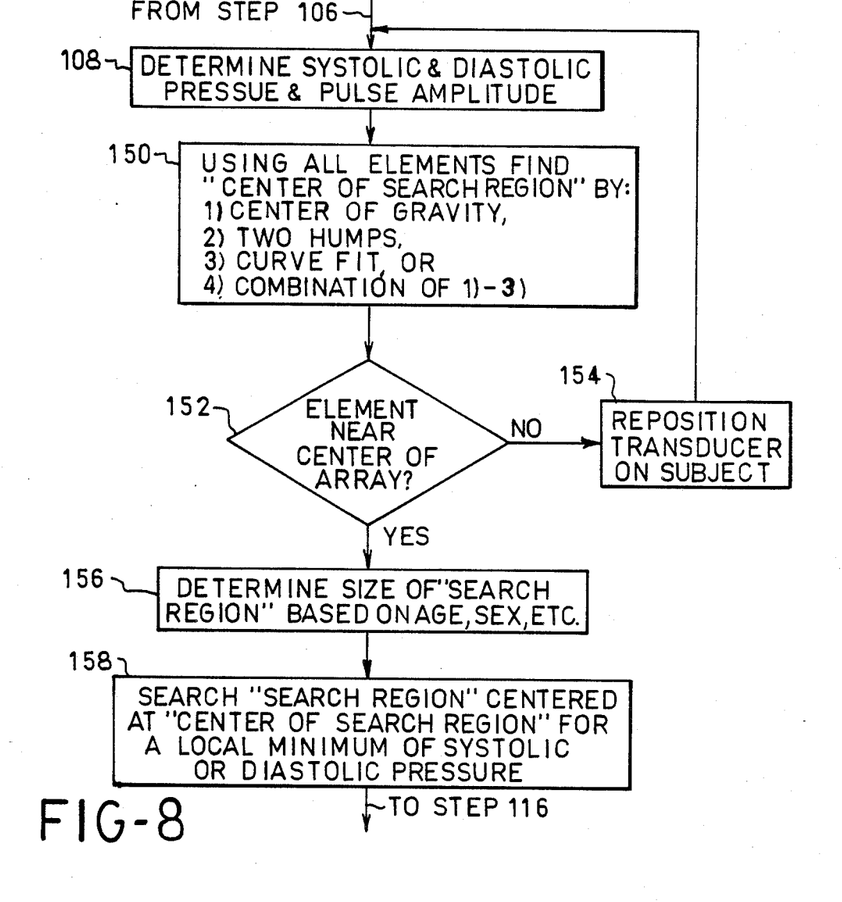
FIG. 8 is a flow chart showing details of the selection of the transducer element to be employed for monitoring blood pressure.

Reference now is made to FIG. 8 wherein step 108 together will details of step 110 of FIG. 5A for selecting the transducer element to be used for monitoring blood pressure are shown. At step 150, the center of the search region is located using pulse amplitude data from all of the transducer elements of the array. A number of different methods for locating the center of the search area may be employed, which methods include, (1) a "center of gravity" method, (2) a "two-humps" method, (3) a "curve fit" method, and, (4) a combination of methods (1)–(3). These methods now will be described in detail.

2. Center of Gravity Method

With the center of gravity method of finding the center of the search region, the center of gravity of the pulse amplitude values for all of the transducer elements in the array is determined, and the transducer element at the center of gravity is selected for the center of the search area. Computation of the center of gravity is a well-known procedure which is readily implemented by computer 62.

The element number corresponding to the "center-of- gravity" of the pulse amplitude distribution, $n_{CG}$, is given by the well-known expression:

$$n_{CG} = \frac{\sum_{n=1}^{n=N} nA_n}{\sum_{n=1}^{n=N} A_n} \quad (1)$$

where n is a variable representing the transducer element number (it is assumed here that the elements are equally-spaced), N is the total number of elements in the tonometer transducer, and $A_n$ is the pulse amplitude measured by the $n^{th}$ transducer element. Using the FIG. 7 data the computed value of $n_{CG}$ is 9.94. This value may be "rounded-off" to the nearest integer, 10, indicating that transducer element 10 is the element at the center of the search area.

3. Two-Humps Method

The two-hump method involves searching the distribution of pulse amplitude values for the maximum, then identifying the second largest local maximum. As noted above, local maxima of pulse amplitude often are located over the edges of the underlying artery. The transducer element midway betewen the two largest local maxima then is taken as the center of the search area. If an even number of transducer elements are included between elements having the two local maxima, then the point midway between the two will be halfway been two adjacent elements. Either of the adjacent elements may be selected as the element at the center of the search area. In FIG. 6, it can see by inspection that there are two local maxima in the pulse amplitude distribution at elements 7 and 12. The point midway between these is halfway between elements 9 and 10 which, for convenience, may be called "element 9.5". In this situation, depending upon the round-off rule used, either element 9 or 10 may be selected as the element at the center of the search area. As noted above, not all subjects exhibit the two-hump pulse amplitude distribution, in which case the two-hump method is not operable. However, when the two-humps are present, they generally identify the two edges of the artery, and the method works well for identifying the center of the search area. This method of identifying the transducer element midway between two largest local maxima of the pulse amplitude distribution is readily implemented using computer 62.

4. Curve Fit Method

The curve fit method of locating the center of the search area includes fitting a polynomial of at least second order to the full set of pulse amplitude versus transducer element number values. A preferred method fits a second-order polynomial to the pulse amplitude data, but third and higher-order polynomials might be used without departing from the teachings of the invention. The dashed line labelled "polynomial" in FIG. 7 shows approximately the curve that would be produced from a second-order polynomial fit to he pulse amplitude data. The point on the graph of the polynomial at which the pulse amplitude is maximum is taken as the center of the search area.

A second-order polynomial fitted to the measured pulse amplitude pressure values may be written as follows:

$$P_m = a_0 + a_1 n + a_2 n^2 \quad (2)$$

wherein:

$P_m$ = measured pulse amplitude, n = the transducer element number, and $a_0$, $a_1$, and $a_2$ are coefficients of the polynomial.

The maximum of this polynomial occurs at an element number, $n_{POLY}$, given by $$n_{POLY} = \frac{-a_1}{2a_2} \quad (3)$$

where $a_1$ and $a_2$ are above-identified polynomial coefficients. After computation, $n_{POLY}$, may be rounded to an integer as described above. The result of applying this process to the FIG. 7 data is the identification of element 10 as the element at the center of the search area. This curve fitting method of locating the center of the search region also is readily implemented by digital computer 62.

5. Combination of Methods

If desired, a combination of the above-described methods may be employed in locating the center of the search region. For example, the double-hump method first may be employed, and if the pulse amplitude distribution includes a pair of local maxima, then the element midway therebetween may be employed. If the distribution does not include a pair of local maxima that are comparably large (e.g. the second maximum is greater than some substantial fraction, say 70%, of the first) then one or more of the other methods may be used.

Alternatively, two or more of the methods may be employed, and results thereof compared. If the same transducer element is identified using the different methods, then that element is selected as the center of the search region. If adjacent elements are identified, then one of them may be selected, and if the elements are widely spaced, then none would be selected and the process would be repeated on the next heartbeat and/or an error or warning message would be issued by the computer 62.

From step 150, decision step 152 is then entered to determined whether or not the element selected for the center of the search area is sufficiently near the center of the transducer array. If it is not, the transducer is repositioned on the subject at step 154, and step 108 is reentered. The process is repeated until the transducer is properly located on the subject. To facilitate positioning of the transducer relative to the underlying artery, the location of the element selected for the center of the search area in the array is displayed. If desired, the exact transducer element 22-1 through 22-19 selected at step 150 may be displayed at step 152. Alternatively, a linear array of, say, three lights may be provided wherein energization of the center light indicates that a centrally located transducer element was selected at step 150. Illumination of either of the end lights would indicate that movement of the transducer to the right or left is required for proper positioning of the transducer array relative to the underlying artery.

C. Determining Size, or Extent, of Search Region

When decision step 152 is affirmative, step 156 is entered where the size, or extent, of the search area is determined. This step involves both knowledge of the dimensions of the pressure sensitive elements of the transducer, and knowledge of the diameter of the subject's artery. Knowledge of the diameter of the subject's artery need not be directly known. Instead, the size of the artery may be estimated from other factors such as the subject's age, sex, height, weight, arm or wrist dimension, or the like, physical, anatomical or physiological information. As noted above, these known factors are entered into computer 62, as through use of keyboard 64.

It is known, for example, that the artery diameter of a male adult generally is larger than that of a female adult which, in turn, is generally larger than that of a young child. An artery diameter on the order of 1.5 mm, 1.1 mm and 0.7 mm for an adult male, an adult female, and a young child, respectively, may be typical in some population groups for a given underlying artery. Weight, height and wrist or arm diameter also provide indications of artery diameter.

Figure 9:
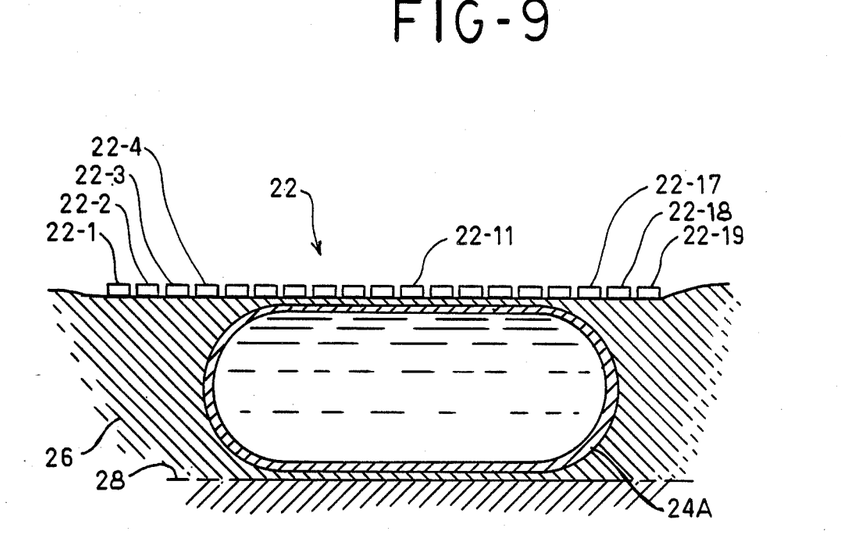
FIG. 9 is a schematic diagram which is similar to that of FIG. 2 but showing only a transducer array and a large underlying artery such as the artery of an adult male.

In FIG. 9, to which reference now is made, the transducer array 22 is shown overlying an artery 24A which is of a male adult, which artery is of substantially larger diameter than artery 24 shown in FIG. 2. The FIG. 2 artery may be that of a child of approximately 12 and, based upon that information, might be assumed to be on the order of 0.7 mm diameter. The larger diameter male adult artery shown in FIG. 9 may be estimated to have a diameter of 1.5 mm.

After the center and extent of the search region have been determined as described above, a search of the region is undertaken. The number of transducer elements employed in this search is dependent upon the effective spacing of the pressure sensitive elements of the transducer. If, for example, the effective center-to-center spacing of elements across the artery is 0.1 mm, then 15 transducer elements would be required to cover the 1.5 mm range for an adult male, 11 elements would be required to cover the 1.1 mm range for an adult female, and 7 transducer elements would be required to cover the 0.7 mm range for a young child. In this example, the region to be searched includes the center element located at step 150 and 7, 5 and 3 elements on either side thereof for the adult male, adult female and young child, respectively. It here will be understood that the transducer elements need not be located in a single straight line, but may be located at staggered positions along parallel lines, for example, to provide for a close "effective" center-to-center spacing of elements across the artery.

D. Selecting Element within Search Region For Monitoring

After the center of the search region is established (steps 150 and 152; item B, above) and the extent of the search region is determined (step 156; item C, above) the transducer element to be used for monitoring blood pressure is selected at step 158. At this step, only those elements that are within the search region are examined in the selection of the element to be used for monitoring.

At this step, the pressure sensitive element within the selected region that generates the signal having a local minimum of at least one of the systolic and diastolic pressures is selected for monitoring. (Here, "local minimum" refers to a local minimum of the plot of systolic, or diastolic, pressure versus transducer element number.) As noted above, for the subject of FIG. 7, transducer element 10 is identified as the center element using the center of gravity and curve fitting methods (methods B2 and B4, above) and either element 9 or 10 is selected using the two-hump method (method B3, above) depending upon the round-off rule employed. In all cases, the elements within one artery radius of the element identified as the center element (either element 9 or element 10) having a local minimum of diastolic pressure is element 10. Element 10 is, in fact, the element centered over the underlying artery. If desired, local minimums of both systolic and diastolic pressures may be checked, in which case the same element normally is identified. This element then is selected for use in measuring blood pressure. However, if different elements are identified, then the process of locating the element to be used may be repeated on subsequent heartbeats until a single element is identified. Alternatively, a warning or error message may be generated by computer 62 when the systolic and diastolic local minima do not occur at the same element.

The invention having been described in detail in accordance with requirements of the Patent Statutes, various other changes and modifications will suggest themselves to those skilled in this art. For example, analog or digital circuit means, or a combination thereof, may be employed for processing the blood pressure waveforms instead of the illustrated digital computer. It is intended that the above and other such changes and modifications shall fall within the spirit and scope of the invention defined in the appended claims.

I claim:

1. A system for the continuous external measurement of blood pressure in an underlying artery of a subject including an array of individual pressure sensitive elements, the length of which array exceeds the diameter of the underlying artery,
   means employing outputs from all elements of the array for identifying one element at a center of a region to be searched,
   user information input means for entering information concerning the subject related to the diameter of the underlying artery into the system,
   means employing said information concerning the subject related to the diameter of the underlying artery for estimating an extent of said region to be searched, and
   means responsive to outputs from only those elements within said region for selecting one element having a local minimum of at least one of the diastolic and systolic pressures on a plot of diastolic or systolic pressure versus transducer element number.

2. A system as defined in claim 1 wherein said selecting means comprises means for selecting the one element having a local minimum of diastolic pressure.

3. A system as defined in claim 1 wherein said selecting means comprises means for selecting the one element having a local minimum of systolic pressure.

4. A system as defined in claim 1 wherein said selecting means includes means for selecting the one element that has both a local minimum of diastolic pressure and a local minimum of systolic pressure.

5. A system for continuous external measurement of blood pressure in an underlying artery of a subject including an array of individual pressure sensitive elements, the length of which array exceeds the diameter of the underlying artery,
   means employing outputs from all elements of the array for identifying one element at the center of a region to be searched, said means including means for finding the center of gravity of the pulse amplitude values for the transducer elements in the array,
   means employing information concerning the subject related to the diameter of the underlying artery for estimating the extent of said region to be searched, and
   means responsive to outputs from only those elements within said region for selecting the one element having a local minimum of at least one of the diastolic and systolic pressures on a plot of diastolic or systolic pressure versus transducer element number.

6. A system for continuous external measurement of blood pressure in an underlying artery of a subject including an array of individual pressure sensitive elements, the length of which array exceeds the diameter of the underlying artery,
   means employing outputs from all elements of the array for identifying one element at the center of a region to be searched, said means including means for identifying two local maxima of the pulse amplitude values and for identifying the element substantially midway between the two local maxima as the element at the center of the region,
   means employing information concerning the subject related to the diameter of the underlying artery for estimating the extent of said region to be searched, and
   means responsive to outputs from only those elements within said region for selecting the one element having a local minimum of at least one of the diastolic and systolic pressures on a plot of diastolic or systolic pressure versus transducer element number.

7. A system for continuous external measurement of blood pressure in an underlying artery of a subject including an array of individual pressure sensitive elements, the length of which array exceeds the diameter of the underlying artery,
   means employing outputs from all elements of the array for identifying one element at the center of a region to be searched, said means including means for fitting a polynomial of at least second order to the pulse amplitude versus transducer element values and for identifying the point on the graph of the polynomial at which it is maximum as the location of the element at the center of the search region, means employing information concerning the subject related to the diameter of the underlying artery for estimating the extent of said region to be searched, and means responsive to outputs from only those elements within said region for selecting the one element having a local minimum of at least one of the diastolic and systolic pressures on a plot of diastolic or systolic pressure versus transducer element number.

8. A system for continuous external measurement of blood pressure is an underlying artery of a subject including an array of individual pressure sensitive elements, the length of which array exceeds the diameter of the underlying artery, means employing outputs from all elements of the array for identifying one element at the center of a region to be searched, means employing information concerning the subject related to the diameter of the underlying artery for estimating the extent of said region to be searched, which information includes at least one of the subject's sex, age, height, weight, arm diameter and wrist diameter, and means responsive to outputs from only those elements within said region for selecting the one element having a local minimum of at least one of the diastolic and systolic pressures on a plot of diastolic or systolic pressure versus transducer element number.

9. A system for the continuous external measurement of blood pressure in an underlying artery of a subject comprising, a pressure sensitive transducer that includes an array of pressure sensitive elements, a group of which elements overlie the artery and with elements extending beyond both edges of the artery, elements of the array producing continuous waveforms which are a function of blood pressure in the underlying artery, means responsive to outputs from the array for obtaining a set of pulse amplitude values for elements of the array, and means for selecting one element which is substantially located adjacent the center of the underlying artery, said selecting means including means for finding the center of gravity of the set of pulse amplitude values.

10. A system for continuous external measurement of blood pressure in an underlying artery of a subject comprising, a pressure sensitive transducer that includes an array of pressure sensitive elements, a group of which elements overlie the artery and with elements extending beyond edges of the artery, elements of the array producing continuous waveforms which are a function of blood pressure in the underlying artery, means responsive to outputs from the array for obtaining a set of pulse amplitude values for elements of the array, and means for selecting one element which is substantially located adjacent the center of the underlying artery, said selecting means including means for identifying the two largest local maxima of the set of pulse amplitude values and for identifying the element substantially midway between the two local maxima as the element which is substantially located adjacent the center of the underlying artery.

11. A system for the continuous external measurement of blood pressure in an underlying artery of a subject comprising, a pressure sensitive transducer that includes an array of pressure sensitive elements, of group of which elements overlie the artery and with elements extending beyond both edges of the artery, elements of the array producing continuous waveforms which are a function of blood pressure in the underlying artery, means responsive to outputs from the array for obtaining a set of pulse amplitude values for elements of the array, and means for selecting one element which is substantially located adjacent the center of the underlying artery, said selecting means including means for fitting a polynomial of at least second order to the set of pulse amplitude values, and means for selecting the point on the graph of the polynomial at which it is maximum as the location of the element which is substantially located adjacent the center of the underlying artery.

12. A method for continuous external measurement of blood pressure in an artery of a subject comprising, positioning a transducer array that includes a plurality of pressure sensitive elements over an underlying artery such that some elements extend beyond both edges of the artery, employing output from all of the elements, identifying one element at substantially the center of the artery, based upon information which includes at least one of the subject's sex, age, height, weight, arm diameter and wrist diameter, estimating the diameter of the underlying artery and the number of elements in a group thereof which substantially overlie the artery, and employing outputs from only those elements in said group thereof, selecting for monitoring the one element having a local minimum of at least one of the diastolic and systolic pressures, where "local minimum" refers to a local minimum on the plot of diastolic or systolic pressure versus transducer element number.

13. A method for the continuous external measurement of blood pressure in an artery of a subject comprising, positioning a transducer array that includes a plurality of pressure sensitive elements over an underlying artery with some elements extending beyond both edges of the artery, for each element of the array obtaining a pulse amplitude value in response to the output from the element to obtain a set of pulse amplitude values, and using the center of gravity of the set of pulse amplitude values for identifying one element which is located substantially at the center of the underlying artery.

14. A method for the continuous external measurement of blood pressure in an artery of a subject comprising, positioning a transducer array that includes a plurality of pressure sensitive elements over an underlying artery with some elements extending beyond both edges of the artery, for each element of the array obtaining a pulse amplitude value in response to the output from that element to obtain a set of pulse amplitude values, identifying the two largest local maxima in the set of pulse amplitude values, and identifying the element substantially midway between these two local maxim as the element located substantially at the center of the underlying artery.

15. A method for the continuous external measurement of blood pressure in an artery of a subject comprising, positioning a transducer array that includes a plurality of pressures sensitive elements over an underlying artery with some elements extending beyond both edges of the artery, for each element of the array obtaining a pulse amplitude value in response to the output from that element to obtain a set of pulse amplitude values, fitting a polynomial of at least second order to the set of pulse amplitude values, identifying the point on the graph of the polynomial at which pulse amplitude is maximum, identifying the element nearest the point on the graph of the polynomial at which the polynomial is maximum as being the element which is substantially located adjacent the center of the underlying artery.

* * * * *